United States Patent
Mohr et al.

(10) Patent No.: US 9,230,703 B2
(45) Date of Patent: Jan. 5, 2016

(54) GRATINGS FOR X-RAY IMAGING, CONSISTING OF AT LEAST TWO MATERIALS

(75) Inventors: Juergen Mohr, Sulzfeld (DE); Joachim Schulz, Karlsruhe (DE); Elena Reznikova, Novosibirsk (RU); Franz Pfeiffer, Garching (DE)

(73) Assignee: KARLSRUHER INSTITUT FUER TECHNOLOGIE, Karlsruhe (DE)

( * ) Notice: Subject to any disclaimer, the term of this patent is extended or adjusted under 35 U.S.C. 154(b) by 416 days.

(21) Appl. No.: 13/703,826

(22) PCT Filed: May 16, 2011

(86) PCT No.: PCT/EP2011/057857
§ 371 (c)(1),
(2), (4) Date: Feb. 25, 2013

(87) PCT Pub. No.: WO2011/157500
PCT Pub. Date: Dec. 22, 2011

(65) Prior Publication Data
US 2013/0148788 A1    Jun. 13, 2013

(30) Foreign Application Priority Data

Jun. 17, 2010  (DE) .................. 10 2010 017 426

(51) Int. Cl.
G21K 1/06        (2006.01)
C25D 5/02        (2006.01)
A61B 6/00        (2006.01)

(52) U.S. Cl.
CPC ............. *G21K 1/067* (2013.01); *C25D 5/022* (2013.01); *G21K 1/06* (2013.01); *A61B 6/508* (2013.01); *G21K 2207/005* (2013.01)

(58) Field of Classification Search
CPC ... G21K 1/06; G21K 1/067; G21K 2207/005; C25D 5/022; A61B 6/508
See application file for complete search history.

(56) References Cited

U.S. PATENT DOCUMENTS

| 4,515,876 | A | 5/1985 | Yoshihara et al. |
| 5,812,629 | A * | 9/1998 | Clauser ........................ 378/62 |
| 7,486,770 | B2 | 2/2009 | Baumann et al. |
| 7,639,786 | B2 | 12/2009 | Baumann et al. |
| 8,165,270 | B2 | 4/2012 | David et al. |
| 2005/0270647 | A1 | 12/2005 | Polack et al. |

(Continued)

FOREIGN PATENT DOCUMENTS

| DE | 202006000330 U1 | 5/2007 |
| DE | 102006037256 A1 | 8/2007 |

(Continued)

OTHER PUBLICATIONS

Holmberg A. et al., Controlled electroplating for high-aspect-ratio zone-plate fabrication, Journal of Vacuum Science and Technology: Part B, AVS / AIP, Melville, New York, NY, US vol. 24, No. 6, (Oct. 31, 2006), pp. 2592-2596.*

(Continued)

*Primary Examiner* — Glen Kao
(74) *Attorney, Agent, or Firm* — Abel Law Group, LLP

(57) ABSTRACT

Gratings for analyzing the interference image in interferometers for phase contrast X-ray tomography, comprising a carrier and grating webs produced from at least two different materials, method for producing the same and use thereof.

20 Claims, 1 Drawing Sheet

(56) References Cited

U.S. PATENT DOCUMENTS

| | | | |
|---|---|---|---|
| 2007/0183579 A1 | 8/2007 | Baumann et al. | |
| 2007/0183583 A1* | 8/2007 | Baumann et al. | 378/145 |
| 2010/0246769 A1 | 9/2010 | David et al. | |
| 2010/0276829 A1 | 11/2010 | Yang et al. | |

FOREIGN PATENT DOCUMENTS

| | | |
|---|---|---|
| DE | 102006037281 A1 | 8/2007 |
| DE | 102008049200 A1 | 4/2010 |
| FR | 830054 A | 7/1938 |
| FR | 2864252 A1 | 6/2005 |
| JP | 2002318283 A | 10/2002 |
| JP | 2006195168 A | 7/2006 |
| JP | 2007206075 A | 8/2007 |
| JP | 2009037023 A | 2/2009 |
| WO | 2007095241 A2 | 8/2007 |

OTHER PUBLICATIONS

C. David et al., "Fabrication of diffraction gratings for hard X-ray phase contrast imaging", Microelectronic Engineering 84, 2007, 1172-1177.

Holmberg A. et al: Controlled electroplating for high-aspect-ratio zone-plate fabrication:, Journal of Vacuum Science and Technology: Part B, AVS / AIP, Melville, New York, NY, US vol. 24, No. 6, Oct. 31, 2006.

Utsumi Y et al: "Soft X-Ray W/BE Multilayer and Its Application to a Diffraction Grating". Review of Scientific Instruments, AIP, Melville, NY, US, vol. 60, No. 7, Part 2B, Jul. 1, 1989, pp. 2024-2026.

Linke Jian et al: "Multilevel microstructures and mold inserts fabricated with planar and oblique x-ray lithography of Su-8 negative photoresist", Proceedings of the SPIE, The International Society for Optical Engineering SPIE, USA, vol. 4557, Sep. 28, 2001, pp. 69-76.

* cited by examiner

GRATINGS FOR X-RAY IMAGING, CONSISTING OF AT LEAST TWO MATERIALS

All documents cited in the present application are incorporated by reference in their entirety in the present disclosure.

FIELD OF THE INVENTION

The present application relates to novel gratings for X-ray imaging by means of phase contrast methods and/or dark field imaging.

TECHNICAL BACKGROUND

Phase contrast imaging using X-rays is based on a grating-based interferometer that uses the Talbot effect for imaging. For this purpose, two gratings are positioned parallel to one another perpendicularly to the X-ray beam. The phase grating g1 consists of lines that cause a phase shift of Pi (or Pi/2) and negligible X-ray absorption. The diffracted rays interfere in accordance with the fractional Talbot effect and an interference pattern arises which is periodic in the directions perpendicular to the grating lines. The second grating serves for analyzing the interference image and is intended to absorb the X-ray radiation as well as possible [absorption grating] (absorption greater than 50% is at least necessary for image evaluation).

The publications by Franz Pfeiffer et al., "Phase retrieval and differential phase-contrast imaging with low-brilliance X-ray sources", Nature Physics, Vol. 2, April 2006, pages 258-261 and "Hard X-ray dark-field imaging using a grating interferometer", Nature Materials, Vol. 7, February 2008, pages 134-137 describe the possibilities of phase contrast X-ray imaging and dark-field imaging using non-coherent X-ray sources. In order to realize these imaging systems, it is necessary to realize grating structures with periods in the range of a few micrometers, the transmission of which over the relevant energy range is less than 50%. The relevant energies are defined by the respective application. Human-medical X-ray examinations of the whole body are usually carried out at working energies of between 50 and 90 keV. In the case of a smaller thickness of the objects to be penetrated, e.g. CTs on children, energies of less than 50 to 70 keV are often also of interest. Thus, lower energies can be used in mammography, for example. The energy is lower in small-animal tests, too. Furthermore, it should be taken into consideration that owing to the radiation emitted by an X-ray tube, even at a high "working energy", radiation below the working energy cannot be avoided.

Gratings used nowadays use gold as material that greatly absorbs the X-rays. Owing to the atomic structure, the absorption of gold decreases by a factor of 4 below an X-ray energy of 80.7 keV. Accordingly, in particular wide-band exposures with X-ray light in a range above and below an X-ray energy of 80 keV do not lead to satisfactory results.

The production of gratings has hitherto been published using gold by means of the LIGA method (Reznikova, E.; Mohr, J.; Boerner, M.; Nazmov, V.; Jakobs, P. J., Soft X-ray lithography of high aspect ratio SU8 submicron structures, Microsystem Technologies, 14 (2008), pages 1683-88 and conformal coating of Si structures with gold in an electrochemical gold bath (C. David, J. Bruder, T. Rohbeck, C. Grünzweig, C. Kottler, A. Diaz, O. Bunk, F. Pfeiffer, Fabrication of diffraction gratings for hard X-ray phase contrast imaging. Microelectric Engineering 84 (2007) 1172-1177), wherein the Si structures are produced by means of a DRIE process.

P. Ramm, M. J. Wolf, A. Klumpp, R. Wieland, B. Wunderle, B. Michel, Through Silicon Via Technology—Processes and Reliability for Wafer-Level 3D System Integration, Proc. 2008 Electronic Components and Technology Conference, pp. 841 discloses technical processes appertaining to silicon technology for producing structures with tungsten.

The production of comparable structures from lead is likewise known (V. Lehmann, S. Rönnebeck, MEMS techniques applied to the fabrication of anti-scatter grids for X-ray imaging, Sensors and Actuators, A95 (2002), 202-207).

The problem of very low absorption of gold below the 80.7 keV edge has not been addressed hitherto.

Object

Accordingly, it is an object of the present invention to provide gratings which, even below the absorption edge of gold at 80.7 keV, in particular between 70 and 80 keV, have higher absorption coefficients in order to enable the radiation to be successfully attenuated even below 80.7 keV.

It is likewise an object of the present invention to provide gratings which are better suited to wide-band exposure with X-ray light, as is the case in a conventional X-ray tube, than the gratings in the previous prior art.

It was furthermore an object of the present invention to provide methods for producing such gratings.

Not least it was an object to find corresponding possibilities for use.

Solution

This object is achieved by gratings comprising a carrier and at least two different materials, in particular metals, and by methods for producing said gratings, and the use thereof.

DEFINITIONS OF TERMS

The abbreviation "LIGA" used in the present invention is a German abbreviation denoting "lithography, electroplating and molding" and is a known method for producing microstructures.

The abbreviation "DRIE" used in the present invention stands for "Deep reactive-ion etching" and is a known method for processing microstructures.

The abbreviation "CVD" used in the present invention stands for "Chemical Vapor Deposition" and is a known method for material deposition.

Gratings within the meaning of the present invention are gratings for analyzing the interference image in interferometers for X-ray imaging by means of phase contrast methods and/or dark field imaging, in particular absorption gratings.

DETAILED DESCRIPTION

The present invention specifically uses materials whose absorption edge for X-ray radiation is below that of gold. They include all materials having an (only slightly) lower atomic number, down to barium. By using these materials, the energy range starting from 67.4 key (Ta) or 69 keV (W) is attenuated better by a multiple using the same layer thickness as gold.

In order to obtain good absorption properties with a wide energy distribution, too, in the context of the present invention a combination of a plurality of materials is used for the gratings, e.g. by one part of the grating being produced from a first material and the other part from a second material, wherein one of the materials has an absorption edge below that of gold.

In this case, in one variant, the first material can be used as a mask in the known LIGA process in order to produce an in-situ aligned LIGA structure and thereby to realize a composite construction.

In one variant of the present invention, the first material is tungsten and the second material is gold.

In one variant of the present invention, it is also possible in this case to replace gold by lead.

In one variant, the present invention relates to the combination of a plurality of materials in gratings in order to be able to specifically attenuate a given spectrum (with the required geometry/period of the grating).

The present invention furthermore relates to the use of tungsten as absorber material for the stated gratings.

The present invention likewise relates to the use of the existing technology "tungsten CVD in DRIE Si trenches" (see P. Ramm et al.) to produce such gratings, and the use of the existing technology "lead casting into etched porous Si structures" (see V. Lehmann et al.) to produce such gratings.

It was a technological challenge to produce a sufficient absorption given the necessary small size of the structures (around 1 μm line width), which requires a large height of the lines and thus a large aspect ratio.

This high absorption required was able to be managed in the context of the present invention by the combination of at least two materials.

For the energy range between 69.5 keV and 80.7 keV, in one variant of the present invention, tungsten is used since gold structures would have to have a height of approximately 176 μm, and tungsten structures only approximately 46 μm (just under 4-fold penetration depth) in order to achieve a transmission of less than 50%. Below 69.5 keV, however, the absorption of tungsten is also relatively low, and so gold affords advantages again in that case.

Accordingly, the combination of these two elements is one variant of the present invention.

A further variant of the present invention is to additionally use at least one further material having an absorption edge at an even lower energy.

In the context of the present invention, in one variant, a specific combination—extremely advantageous for the application—of materials having different absorption edges and optionally additionally adapted heights was found, in particular by the combination of gold and tungsten.

For wide-band applications, in the context of the present invention, by adapting the relative heights of at least two selected materials, preferably gold and tungsten, over the entire energy range it is possible to set the absorption properties so as to result in a sufficient image quality.

In one variant preferred according to the invention, the combination of 100 μm Au and 22 μm W yields an absorption of better than 50% over the entire energy range. Therefore, in medical analysis, it is possible to choose the X-ray energy even in the range of 70 to 80 keV such that the tissue samples to be examined are represented as sensitively as possible.

In principle, it is possible to produce gratings having a small width of up to 1 μm in gold with heights of up to 100 μm such that above 80.7 keV to approximately 110 keV the transmission is significantly less than 50%. From a present-day perspective, larger thicknesses can be realized only with difficulty, however, since the stability of the form decreases with the third power of the height and extremely small loads leads to bending of the webs.

In the range between 69.5 and 80.7 keV, by contrast, a transmission of less than 50% can be achieved by means of a tungsten structure having a thickness of approximately 46 μm. What is problematic, however, is that the transmission of said tungsten structure is higher in the other energy ranges and thus represents a poorer grating there. Moreover, there are no known methods that makes it possible to pattern tungsten with micrometer dimensions and an aspect ratio of 100.

The problem of the high transmission in the case of gold in the range between 69.5 and 80.7 keV can be solved whilst maintaining a high absorption outside this range by means of the present invention, namely the combination of different materials.

Accordingly, the present invention relates, in particular, to gratings comprising a carrier and at least two materials, in particular metals.

In this case, variants of the present invention are such gratings which have a layer structure selected from the group consisting of
i) carrier/ML1/ML2,
ii) carrier/ML1/ML2/ML3,
iii) carrier/ML1/ML2/ML3/ML4,
iv) carrier/ML1/ML2/ML3/ML4/ML5
v) ML1/carrier/ML2,
vi) ML1/ML2/carrier/ML3,
vii) ML1/ML2/carrier/ML3/ML4,
viii) ML1/ML2/ML3/carrier/ML4,
ix) ML1/ML2/ML3/carrier/ML4/ML5,
preferably layer structure i) or v),
wherein the designation ML stands for material layer, more particularly metal layer.

In this case, layer in the context of the present invention does not necessarily mean a planar, flat surface. The gratings of the present invention are based, as seen from the side, for example, on comb-like structures. Accordingly, a layer can consist of lamellae arranged alongside one another or of, as seen from the side, comb-like structures (corresponding to base plate and teeth or lamellae), whereas other layers independently thereof can be flat plates.

This is sufficiently known to the person skilled in the art and, in the methods according to the invention, also inevitably arises proceeding from the techniques employed (also cf. FIG. 2).

One variant of the present invention in this case involves gratings which consist of a carrier and exactly two metals, wherein the metals are preferably gold and tungsten.

A further variant of the present invention in this case involves gratings having the layer structure carrier/Au/W or carrier/W/Au or W/carrier/Au, preferably carrier/W/Au.

One variant of the present invention in this case involves gratings which consist of a carrier and exactly three metals, wherein two of the metals are preferably gold and tungsten.

In one variant, the carriers of the gratings according to the invention are selected from the group of materials having low absorption.

A low absorption in the case of the carrier material is understood to mean that the absorption is only slight relative to the absorption by the metals. This property of the carrier material is familiar to the person skilled in the art and can, if appropriate, if not already known to said person anyway, be taken from table works in a simple manner.

Preferably all metals up to atomic number 30 with a suitably selected layer thickness are suitable.

In one variant, the carriers consist of silicon and/or compounds thereof such as e.g. silicon nitride, preferably silicon.

In another variant, the carriers consist of polymers, in particular polyimides.

In a further variant, the carriers consist of metals having a low atomic number of less than or equal to 30, in particular titanium.

In an additional variant, the carriers consist of a combination of silicon or silicon compounds, polymers and/or materials having a low atomic number.

In particular, through a combination of 22 µm tungsten and 100 µm gold, it is possible to reduce the transmission in the range of 69.5 to 80.7 keV compared with a 100 µm thick gold structure by more than 10% (approximately 16%) to less than 50%. In the other ranges, it is approximately 5% less than the transmission of the pure 100 µm thick gold.

For the case of 100 µm gold and 22 µm tungsten, the transmission is lower for the entire energy range.

Particularly preferred configurations of the present invention are combinations of Au and W in the height ratio of 2:1 to 6:1.

Examples according to the invention are
100 µm Au and 22 µm W
90 µm Au and 30 µm W
80 µm Au and 40 µm W As absorbent materials, in the context of the present invention, alongside the combination of W and Au, in variants it is also possible to combine the following materials:
Pb/Pt, Pb/W, Pb/Ta, Au/Ta, Au/Ba, Au/BaF$_2$, Au/Gd$_2$O$_2$S One variant according to the invention for producing the gratings according to the invention comprising two materials, in particular metals, is a method I) comprising the following steps, preferably consisting of the following steps:
- a1) the grating structure is worked, preferably etched by DRIE, into a carrier wafer, preferably a silicon wafer,
- b1) these grating structures are filled with a first material, preferably W, preferably by means of CVD,
- c1) the first material deposited on the surface, preferably W, is removed, preferably by back-sputtering and the wafer, preferably silicon wafer, is thinned back on the rear side, preferably by a lapping process, and clamped onto a frame if appropriate for mechanical stabilization,
- d1) onto the front side (composite structure first material/wafer) a metallic layer is applied, which later serves as an electroplating start layer,
- e1) a negative resist is applied on said layer and
- f1) is patterned in accordance with the LIGA method with X-ray radiation from the rear side,
- g1) and the freely developed trenches are filled with a second material.

In this case, in this variant, the first material/wafer structure serves as a mask for the negative resist, i.e. the radiation is transmitted through the thinned wafer from the rear side. The structures of the first material constitute the absorber and allow the production of trench structures in the negative resist. The latter are filled electrolytically with the second material, preferably Au. By virtue of the integrated mask of the first metal, the structures of the second material become situated above the structures of the first material without further alignment.

Alternatively, the configurations
- d1.2) onto the rear side (composite structure first material/wafer) a metallic layer is applied, which later serves as an electroplating start layer, and
- f1.2) is patterned in accordance with the LIGA method with X-ray radiation from the front side are possible for this production method.

A second variant according to the invention for producing the gratings according to the invention comprising two materials, in particular metals, is a method II) comprising the following steps, preferably consisting of the following steps:
- a2) corresponding to a1)
- b2) corresponding to b1)
- c2) corresponding to c1)
- d2) corresponding to d1) or d1.2)
- e2) a positive resist is applied on said layer and
- f2) is patterned via an aligned mask in accordance with the RIGA method with X-ray radiation from the front side or else the rear side.

These two methods I) and II) make it possible very well to produce composite structures, in particular gratings, made from a first and a second material, preferably tungsten and gold.

In variants of methods I) and II) of the present invention, the following features are applied, wherein the different respective ranges of the individual features are independent of arbitrary ranges of other features (i.e. it is possible, for example, to combine the most highly preferred ranges of individual steps with the broader ranges of other steps):
- a1), a2) silicon layer thickness of 150 to 1000 µm, preferably of 500 to 800 µm, in particular of 500 to 700 µm, or of 180 to 220 µm
- a1), a2) DRIE to a depth of 20 to 100 µm, preferably of 30 to 70 µm, in particular of 30 to 50 µm
- b1), b2) conformal coating thickness of 0.5 to 6 µm, preferably of 1 to 3 µm
- c1), c2) back-lapping to a maximum of 100 µm, preferably a maximum of 70 µm, in particular a maximum of 50 µm
- d1), d2) material layer thickness of 0.05 to 10 µm, preferably of 0.3 to 3 µm, in particular of 1 to 3 µm
- d1), d2) material of the metallic layer selected from the group consisting of Ti, Cr, Ti/Au, Ti/Au, Cr/Au, Cu, Ag and mixtures thereof,
- e1) layer thickness of negative resist of 30 to 1000 µm, preferably of 40 to 200 µm, in particular of 50 to 150 µm
- e1) negative resist selected from the group consisting of chemically amplified resists, in particular epoxide-based resists, polyimides and mixtures thereof
- e2) layer thickness of positive resist of 30 to 1000 µm, preferably of 40 to 200 µm, in particular of 50 to 150 µm,
- e2) positive resist selected from the group consisting of acrylates, phenolic resins and mixtures thereof.

The substances already described above as carrier are used as carrier or wafer.

After these methods, further layers can be applied by the corresponding method steps.

The present invention likewise relates to corresponding methods.

As an alternative to the two methods I) and II), the structure of the second metal can also be produced on the rear side of the thinned substrate. In this case, after the wafer has been thinned, said wafer is applied to a frame, such that the underside of the wafer is exposed. Said underside is then coated with the negative resist and the lithography and electroplating process is correspondingly carried out. The advantage of this variant is that the silicon can be thinned to significantly less than 50 µm, if necessary for reasons appertaining to X-ray lithography; this accordingly corresponds to method III)

comprising the following steps, preferably consisting of the following steps:
- a3) the grating structures are worked into a carrier wafer,
- b3) these grating structures are filled with a first metal, c3) the first metal deposited on the surface is removed by a lapping process, d3) the wafer is applied to a frame, such that the underside of the wafer is exposed, the wafer is thinned back on the rear side and a metallic layer is applied, e3) a negative resist is applied on said underside and f3) is patterned in accordance with the LIGA method, g3) and the freely developed trenches are filled with a second material.

Alternatively, in step e3) a positive resist can be applied and then irradiated in accordance with the LIGA method via a mask in the manner aligned with respect to the first structure.

This method III) also makes it possible to produce very well composite structures, in particular gratings, made from a first and a second material, preferably tungsten and gold.

After this method, too, further layers can be applied by the corresponding method steps.

The present invention likewise relates to corresponding methods.

The gratings according to the invention can be used in X-ray-based systems appertaining to medical technology (e.g. X-ray tomography), in the non-destructive testing of materials and components, in pharmaceutical screening, in baggage and mail scanners, in gantry units of computer tomographs, in X-ray optics in micro-CT apparatuses, in X-ray optical systems for medical radiography (mammography) or angiography, in tumor therapy examinations for small animals, in X-ray imaging in the broadest sense (tomography, radiography, light diffuser gratings, material investigations).

The different configurations of the present invention, e.g. but not exclusively those of the different dependent claims, can be combined with one another arbitrarily here.

DESCRIPTION OF THE FIGURES

The figures are not true to scale. For reasons of clarity and for simpler illustration, some features of the invention may be illustrated with an exaggerated size or in a schematic form; likewise, some details of conventional or known elements may accordingly not be illustrated.

Figure 1:
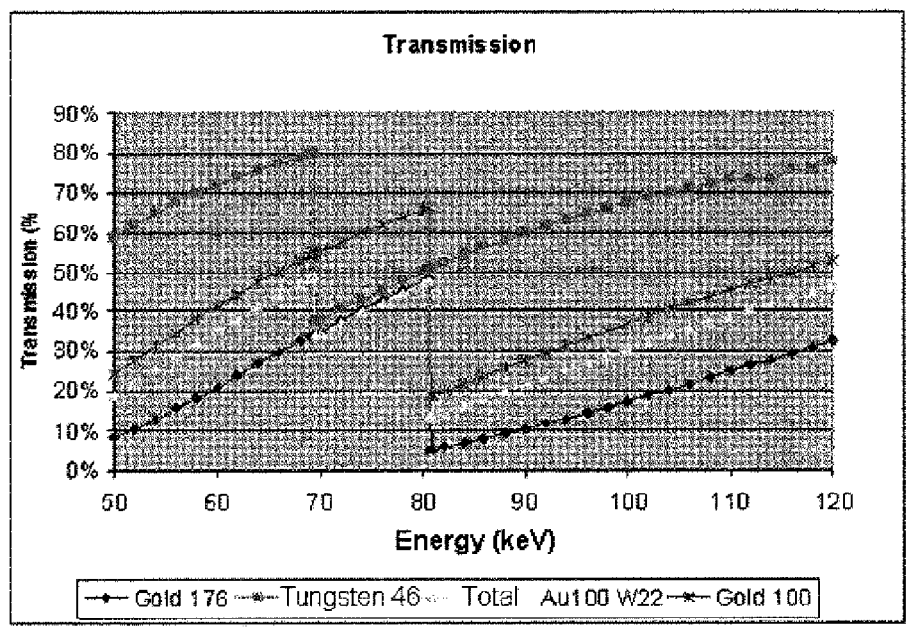
FIG. 1 shows that in the case of structures in gold having thicknesses of 100 μm, above 80 keV to approximately 110 keV, the transmission is significantly less than 50% (purple curve; asterisk symbols). As can be discerned, the transmission below 80 keV rises abruptly and is even more than 60%.

It can furthermore be seen from FIG. 1 that in the range between 70 and 80 keV a transmission of less than 50% can be achieved by a 46 μm thick tungsten structure (pink curve; square symbols in FIG. 1), but the transmission of said tungsten structure is higher in the other energy ranges. The yellow curve, triangular symbols, shows that a combination of 22 μm tungsten and 100 μm gold reduces the transmission in the range of 70 to 80 keV compared with 100 μm gold structure by more than 10% to less than 50%. In the other ranges, the transmission is approximately 5% lower than the transmission of the pure 100 μm thick gold.

Furthermore, it can be seen that only an increase in the layer thickness of the gold to 176 μm (blue curve, diamond-shaped symbols) reduces the transmission to less than 50% in the entire energy range.

Figure 2:
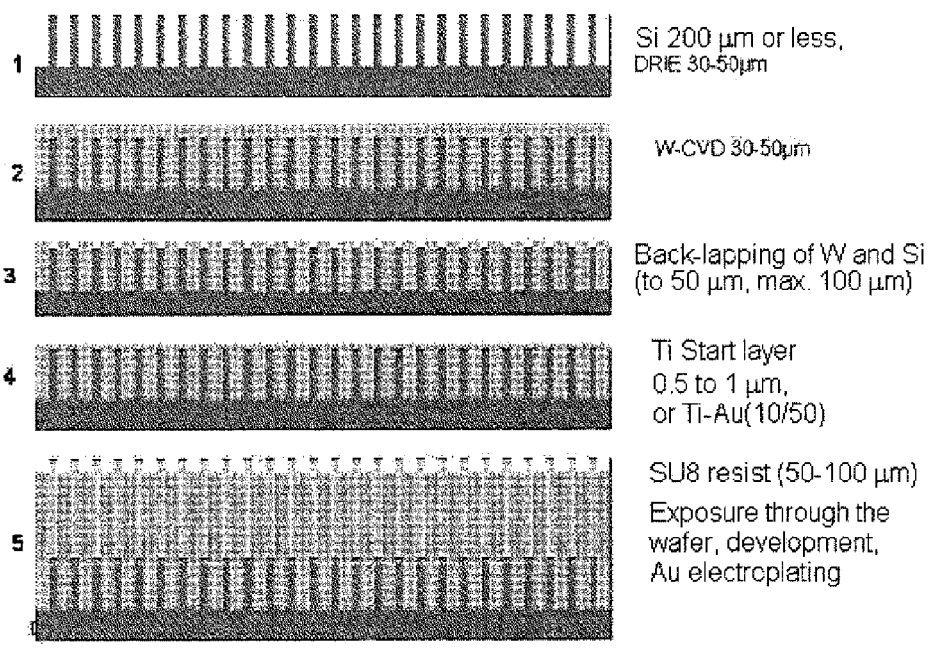

FIG. 2 illustrates the production of gratings according to the invention on the basis of the combination of two metals, in accordance with variant I) according to the invention.

What is claimed is:

1. An absorption grating, wherein the grating is suitable for analyzing an interference image in an interferometer for x-ray imaging by a phase contrast method and/or dark field imaging and comprises a carrier and at least two materials which absorb x-rays, the at least two materials comprising (a) gold or lead and (b) a material comprising an element with an atomic number lower than that of gold and down to that of barium, and wherein the grating has a layer structure selected from (i) carrier/ML1/ML2, (ii) carrier/ML1/ML2/ML3, (iii) carrier/ML1/ML2/ML3/ML4, (iv) carrier/ML1/ML2/ML3/ML4/ML5, (v) ML1/carrier/ML2, (vi) ML1/ML2/carrier/ML3, (vii) ML1/ML2/carrier/ML3/ML4, (viii) ML1/ML2/ML3/carrier/ML4, (ix) ML1/ML2/ML3/carrier/ML4/ML5, wherein ML stands for material layer or metal layer.

2. The grating of claim 1, wherein the at least two materials are both metals.

3. The grating of claim 1, wherein the grating has a layer structure (i).

4. The grating of claim 1, wherein the grating has a layer structure (v).

5. The grating of claim 1, wherein the grating consists of a carrier and exactly two materials.

6. The grating of claim 5, wherein the two materials are gold and tungsten.

7. The grating of claim 6, wherein a ratio of a layer thickness of W to a layer thickness of Au is from 1:2 to 1:6.

8. The grating of claim 7, wherein the layer structure is carrier/Au/W or W/carrier/Au.

9. The grating of claim 7, wherein the layer structure is carrier/W/Au.

10. The grating of claim 1, wherein the at least two materials comprise a combination selected from Pb/Pt, Pb/W, Pb/Ta, Au/Ta, Au/Ba, Au/BaF$_2$, Au/Gd$_2$O$_2$S.

11. The grating of claim 1, wherein the carrier is selected from one or more of silicon, silicon compounds, polymers, and materials having a low atomic number.

12. A method for producing the grating of claim 1, wherein the method comprises:

(a1) working a grating structure into a carrier wafer, (b1) filling the grating structure with a first material, (c1) removing first material deposited on a surface and thinning the wafer back on a rear side, (d1.1) applying onto a front side (composite structure first material/wafer) a metallic layer, or (d1.2) applying onto a rear side (composite structure first material/wafer) a metallic layer, which layer later serves as an electroplating start layer, (e1) applying a negative resist on the metallic layer and patterning the resist with X-ray radiation in accordance with a LIGA method (f1.1) from a front side, or (f1.2) from a rear side, (g1) filling freely developed trenches with a second material.

13. A method for producing the grating of claim 1, wherein the method comprises:

(a2) working a grating structure into a carrier wafer, (b2) filling the grating structure with a first material, (c2) removing first material deposited on a surface and thinning the wafer back on a rear side, (d2.1) applying onto a front side (composite structure first material/wafer) a metallic layer, or (d2.2) applying onto a rear side (composite structure first material/wafer) a metallic layer, which layer later serves as an electroplating start layer, (e2) applying a positive resist on the metallic layer, and (f2) patterning the positive resist with X-ray radiation from the front side or rear side via an aligned mask in accordance with a LIGA method.

14. A method for producing the grating of claim 1, wherein the method comprises:
- (a3) working a grating structure into a carrier wafer,
- (b3) filling the grating structure with a first material,
- (c3) removing first metal deposited on a surface by a lapping process,
- (d3) applying the wafer to a frame, such that an underside of the wafer is exposed, thinning back the wafer on a rear side, and applying a metallic layer,
- (e3) applying a negative resist on the underside of the wafer, and
- (f3) patterning the negative resist in accordance with a LIGA method,
- (g3) filling freely developed trenches with a second material.

15. The method of claim 14, wherein in (e3) a positive resist is applied and is irradiated in accordance with the LIGA method via a mask in a manner aligned with respect to a first structure.

16. A system, unit or apparatus selected from an X-ray-based system appertaining to medical technology, a gantry unit of a computer tomograph, an X-ray micro-CT apparatus, an X-ray optical system for medical radiography (mammography) or angiography, and a baggage or mail scanner, wherein the system, unit or apparatus comprises the grating of claim 1.

17. A method of non-destructive testing of materials and components or of pharmaceutical screening, wherein the method comprises analyzing an interference image in an interferometer for x-ray imaging by a phase contrast method and/or dark field imaging employing the grating of claim 1.

18. A method of tumor therapy examination for small animals, wherein the method comprises analyzing an interference image in an interferometer for x-ray imaging by a phase contrast method and/or dark field imaging employing the grating of claim 1.

19. A method of X-ray imaging, wherein the method comprises analyzing an interference image in an interferometer for x-ray imaging by a phase contrast method and/or dark field imaging employing the grating of claim 1.

20. The method of claim 19, wherein the X-ray imaging comprises or involves tomography, radiography, a material investigation, or a light diffuser screen.

* * * * *